United States Patent [19]

De Jonge et al.

[11] 4,147,659
[45] Apr. 3, 1979

[54] NOVEL ANTIOXIDANT COMPOSITION AND PROCESS FOR MAKING THE SAME

[75] Inventors: Cornelis R. H. De Jonge, De Steeg; Egenius A. Giezen, Rheden, both of Netherlands

[73] Assignee: Akzona Incorporated, Asheville, N.C.

[21] Appl. No.: 903,262

[22] Filed: May 5, 1978

Related U.S. Application Data

[62] Division of Ser. No. 729,497, Oct. 4, 1976.

[30] Foreign Application Priority Data

Oct. 4, 1975 [NL] Netherlands .......................... 7511698

[51] Int. Cl.² ...................... C09K 15/08; C09K 15/14; C09K 15/30
[52] U.S. Cl. ................................. 252/400 A; 252/402; 252/404; 252/406; 260/45.7 PH; 260/45.8 NT; 544/219
[58] Field of Search ................... 252/400 A, 402, 404, 252/406, 47.5; 544/219; 260/45.8 NT, 45.7 PH

[56] References Cited

U.S. PATENT DOCUMENTS

| | | | |
|---|---|---|---|
| 3,255,191 | 6/1966 | Dexter et al. | 544/219 |
| 3,334,046 | 8/1967 | Dexter | 252/47.5 |
| 3,729,471 | 4/1973 | Robin et al. | 544/219 |

FOREIGN PATENT DOCUMENTS 1419632  12/1975  United Kingdom ...................... 544/219

Primary Examiner—Benjamin R. Padgett
Assistant Examiner—Irwin Gluck
Attorney, Agent, or Firm—Francis W. Young; Robert F. Green

[57] ABSTRACT

A novel antioxidant composition and a method for making the same is disclosed. Said composition comprising,

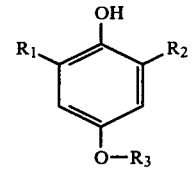

wherein $R_1$ and $R_2$ independently are selected from the group consisting of tertiary butyl, isopropyl, cyclohexyl, and phenyl, and $R_3$ is a substituted triazine of the formula,

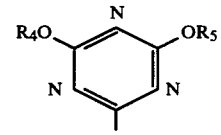

wherein $R_4$ and $R_5$ independently are selected from the group consisting of organic radicals having at least one non-aromatic carbon atom, which non-aromatic carbon atom is attached to an oxygen atom connecting said radical with the triazine group.

5 Claims, No Drawings

NOVEL ANTIOXIDANT COMPOSITION AND PROCESS FOR MAKING THE SAME

This is a division, of application Ser. No. 729,497, filed Oct. 4, 1976.

BACKGROUND OF THE INVENTION

This invention relates to a novel antioxidant composition and the process for making the same. Many phenolic type antioxidants have been known heretofore. For example, an article by A. R. Patel et al, in Journal of Applied Polymer Science 16 (1972) at pages 2751–2763, describes the compound 6-(4-hydroxy-3,5-di-tertiarybutylanilino)-2,4-bis(n-octylthio)-1,3,5 triazine, which is mentioned as the most effective antioxidant for the stabilization of polybutadiene rubber.

U.S. Pat. No. 3,334,046 also teaches the existance of 2,6-disubstituted phenolic antioxidants which are in the 4-position attached to a triazine compound. British patent specification No. 1,345,988 teaches a process for the preparation of compounds having the formula

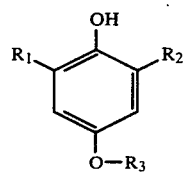

wherein $R_1$ and $R_2$ are tertiary butyl, isopropyl, cyclohexyl, or phenyl and $R_3$ is an organic radical. The preparation of such compounds generally comprises adding, dropwise, concentrated sulphuric acid to a heated solution of hydroquinone and the alcohol derived from $R_3$. When the alcohol derived from $R_3$ contains 10 or more carbon atoms such a process is very difficult to practice commercially due to the formation of many by-products and the very slow reactionary. Thus, when $R_3$ contains 10 or more carbon atoms, it is preferred to use a process in which the hydroquinone is reacted with an alkyl bromide in the presence of a weak base such as potassium bicarbonate and then a solvent such as cellosolve. Compounds in which $R_3$ contains an alkyl group with 10 or more carbon atoms is especially suitable for protecting polyolefins from oxidation, not only during initial processing, but also thereafter. The compound 6-(4-hydroxy-3,5-di-tertiarybutylanilino)-2,4-bis(n-octylthio)-1,3,5 triazine, which is described in the article by A. R. Patel et al, is marketed by CIBA-GEIGY under the trade name Irganox 565. For the stabilization of polypropylene, however, it is preferred to use tetrakis [3-(3,5-di-tertiarybutyl-4-hydroxyphenyl)propionyloxymethyl]methane, which is marketed by CIBA-GEIGY under the trade mark Irganox 1010. The foregoing is not surprising, considering the fact that the triazine disclosed in the article by Patel et al is very sensitive to oxidation and the two thioether groups have little resistance to U.V. degradation. The oxidation product of said triazine compound is colored, making the triazine compound unsuitable for many applications. Moreover, the permanent protection of various polymers, such as polypropylene, is difficult to affect with such triazine compounds due to the instability of the thioether groups upon exposure to the U.V. light of the solar spectrum.

DESCRIPTION OF THE INVENTION

The present invention provides a new class of compounds which do not have the disadvantages of the known triazine compounds, which may also be readily and homogeneously distributed in polymers such as polyolefins. The preparation of such compounds may also be achieved without great difficulty. Furthermore, the compounds of the present invention are especially suitable for protecting polyolefins from oxidation during both initial processing and thereafter. The compounds of the present invention comprise a composition having the formula

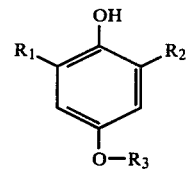

wherein $R_1$ and $R_2$ independently are selected from the group consisting of tertiary butyl, isopropyl, cyclohexyl, and phenyl, and $R_3$ is a substituted triazine of the formula,

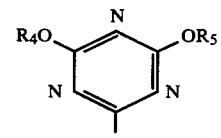

wherein $R_4$ and $R_5$ independently are selected from the group consisting of organic radicals having at least one non-aromatic carbon atoms, which non-aromatic carbon atom is attached to an oxygen atom connecting said radical with the triazine group. The present invention also provides a process for making the aforementioned compositions. Such a process comprises reacting a compound having the structure

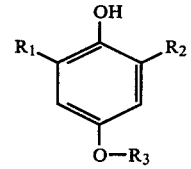

wherein $R_1$ and $R_2$ independently are selected from the group consisting of tertiary butyl, isopropyl, cyclohexyl, and phenyl and $R_3$ is hydrogen, in an organic solvent with an approximately equimolar amount of a compound having the formula

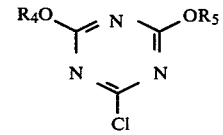

wherein $R_4$ and $R_5$ independently are selected from the group consisting of organic radicals having at least one non-aromatic carbon atom, which non-aromatic carbon atom is attached to an oxygen atom connecting said radical with the triazine group. The reaction is carried out in the presence of a strong base in a molar amount which is at least equivalent to that of the triazine compound.

After the mixture has been heated, preferably to between 40° and 100° C., it is neutralized with acid upon completion of the reaction, and extracted with, for example, methylene chloride, and the reaction product is obtained by evaporation of the extraction liquid. Examples of suitable organic solvents for carrying out the addition reaction include ketones, such as acetone, methylethylketone, and methylisobutyl ketone.

The triazine compound which is used in the addition reaction may be prepared by bringing an alcohol, in the presence of an acid acceptor, in reaction with cyanuric chloride, and subsequently separating off the resulting reaction product. If $R_4$ and $R_5$ represent a methyl group, such a process will be readily suitable. A process such as that described is detailed in an article by O. Diels et al in Ber., 36, 3191 (1903). In such a process 1 molar equivalent of cyanuric chloride, in the presence of 2 molar equivalents of sodium bicarbonate, is reacted with a very large excess of methanol, which also acts as a solvent. After heating with refluxing, cooling, and diluting with water, a crude reaction product may be filtered off.

For the preparation of compounds where $R_4$, $R_5$, or both represent a group with 3 or more carbon atoms, the foregoing process is not suitable. In such an instance the above-indicated process should be modified so that (1) for the acid acceptor a compound having a pKb23 is used, (2) for the molar ratio of acid acceptor to cyanuric chloride, a value of at least two is chosen, (3) for the molar ratio of alcohol to cyanuric chloride a value of about two is chosen, and (4) the reaction is carried out in a solvent which is inert to the reaction components. Examples of suitable inert solvents are dioxan, tetrahydrofuran, di-methoxyethane, di-n-butyl ether, toluene, benzene, acetone, methyl-ethyl ketone, or preferably, methyl isobutyl ketone. Suitable acid acceptors include any substance with a $pKb \geq 3$, such as KOH, CaO, borax, $Na_3PO_4$ and $K_3PO_4$ Powdered sodium hydroxide is preferred.

If $R_4$ and $R_5$ represent groups having a relatively high molecular weight, such as lauryl or stearyl, it is preferred that the alcohol is used in less than stoichiometric amount. The temperature during the reaction is preferably below 50°C. and most preferably between 15° and 30° C. As indicated above, $R_4$ and $R_5$ are organic radicals having at least one non-aromatic carbon atom each. The non-aromatic carbon atom is attached to the triazine group through a bridging oxygen atom. $R_4$ and $R_5$ may, of course, carry substituents provided that said substitutents remain inert under the reaction conditions employed, and do not unfavorably influence the stabilizer compositions according to the invention. Examples of such substituents include alkoxy groups, halogen atoms, aromatic groups, such as phenyl and naphthyl, and heterocyclic groups, as in furfuryl alcohol.

In a preferred embodiment of the present invention $R_1$, $R_2$, or both, represent a phenyl group and $R_4$, $R_5$, or both represent an alkyl group with 8 to 20 carbon atoms. In the stabilization of objects made of polyolefins, such as polypropylene, polyethylene, and ABS rubber, such compounds are found to display a high degree of activity, both as a result of their very homogeneous distribution in such polymers and the presence of a phenyl group. Said activity, however, is especially high if the antioxidants of the present invention are used in combination with a secondary antioxidant which also has a low volatility. The weight ratio of primary antioxidants to secondary antioxidants may vary between wide limits. Favorable results are generally obtained if the weight ratio of secondary antioxidant to primary antioxidant is between 2:1 and 10:1. However, it is also possible to employ a higher or lower ratio, and a man skilled in the art may easily establish the optimum concentration and ratio for each variant structure of the antioxidants employed. The same is also true for determining the percentage of stabilizer to be employed in the substance to be stabilized.

Compounds which display a secondary antioxidizing effect are, for example, the $\beta$-activated thio ethers discussed, for example, in British patent specification No. 1,345,988. Examples of other secondary antioxidants are phosphites, thiophosphites, and especially phosphites with a $—S—CH_2CH_2—Y$ group where Y represents a $\beta$-activating group. Preferably thio ethers with a $\beta$-activating group, such as dilauryl thiodipropionate (DLTDP) and distearyl thiodipropionate (DSTDP) are employed, due to their low volatility and satisfactory activity in stabilizer compositions. Good results may also be obtained by the use of trilauryl trithiophosphite and tristearyl trithiophosphite. Another very active secondary antioxidant is tetrakis ($\beta$-carbo-octoxyethylthio)-4,4'isopropylidene-diphenyl-diphosphite. Other suitable phosphorus compounds are those mentioned in U.S. Patent Nos. 3,039,993 and 3,682,879. The preferred compounds contain a phosphorus atom which is attached to at least sulphur atom, is preferably $\beta$-activated.

The amounts in which the antioxidants for the present invention are employed will vary widely and depend upon whether a secondary antioxidant is employed, and if so, the nature thereof. When a synergistic mixture is employed, the amounts are always very small and generally vary from about 0.01 to about 10% by weight, calculated on the amount of organic compound to be stabilized. Amounts larger than about 10% by weight may be incorporated in substances to be stabilized, although such amounts generally do not lead to sufficient improvement of the antioxidizing effect to justify the increase in expense. Large amounts of antioxidant may also have an unfavorable effect on other properties of the material to be stabilized, and thus should be avoided. Optimum results are, as a rule, found to be obtained with the use of an amount in the range of from about 0.03 to about 1% by weight.

The following examples are presented as illustrative of the invention. It is not intended that the invention should be limited to the specific embodiments illustrated therein. In the following examples the effectiveness of the various stabilizer compositions were determined in polypropylene films having a thickness of 150 $\mu$m obtained by extrusion for from 2 to about 3 minutes at 180° to 190° C. A number of such films were heated over a prolonged period in an air circulation oven at 140° to 120° C. The decrease of the amount of primary antioxidant present was determined by U.V. absorption. When the amount of antioxidant was used up, which could be readily determined with the aid of the U.V. measurement, the polymer rapidly became brittle. The induction time mentioned in the examples is the time during which the film maintained its favorable properties. Subsequently, oxidative decomposition set in and the film rapidly lost its mechanical properties.

EXAMPLE I

Preparation of 6-(4-hydroxy-3,5-diphenylphenoxy)-2,4-dilauroxys-triazine

To a solution of 18.4 g (0.1 mole) of cyanuric chloride in methylisobutyl ketone there was added 14.4 g (0.36 moles) of powdered sodium hydroxide over a period of 10 minutes at a reaction temperature between 32° and 37° C. After 45 minutes the reaction was completed. Following acidification with concentrated hydrochloric acid and heating to 80° C., the reaction mixture was freed of NaCl by filtration. Further treatment of the reaction mixture resulted in a product having a melting point in the range of from 43.5° to 44.9° C.

In a 500 ml-three-necked flask 4.8 g (0.01 mole) of the 2-chloro-4,6-dilauroxy-s-triazine prepared above, were mixed with 2.6 g (0.01 mole) of 2,6-diphenyl hydroquinone. After rinsing with nitrogen, 150 ml of acetone were added, followed by adding dropwise, with vigorous stilling, 0.4 g (0.01 mole) of NaOH dissolved in 7 ml of water, at 20° C. The solution then assumed an orange-yellow color, which largely disappeared upon heating the reaction mixture for a longth of time under reflux. After completion of the reaction, the contents of the flask were poured into 100 ml of ice water containing 2 ml of hydrochloric acid. The organic layer was extracted three times with methylene chloride, after which the combined extracts were washed and dried. After concentration of the organic layer by evaporation a product was obtained which crystallized out after a length of time (melting point 18°–20° C.).

With nuclear magnetic resonance (NMR), infrared spectroscopy (IR) and mass spectroscopy it could be demonstrated that the structure of the compound obtained corresponded to that of the compound 6-(4-hydroxy-3,5-diphenylphenoxy)-2,4-dilauroxy-s-triazine.

EXAMPLE II

Preparation of 6-(4-hydroxy-3,5-diphenylphenoxy)-2,4-dimethoxy-s-triazine

In a mixture of 400 ml of methanol and 40 ml of water there were added 148 g (0.8 moles) of cyanuric chloride at a temperature of 30° C. After 7 hours' reaction time, the reaction mixture was extracted with methylene chloride. After washing with water until neutral, the extract was dried with MgSO$_4$ and concentrated by evaporation. After recrystallization from petroleum ether (boiling point 40°–60° C.), 126 g of 2,4-dimethoxy-6-chloro-s-triazine having a melting point between 74.2° and 76.2° C. were obtained.

The preparation of the title product was carried out in the manner indicated in Example I. The resulting reaction product had a melting point in the range of from 155.8° to 157° C.

EXAMPLE III

Preparation of 6-(4-hydroxy-3,5-diphenyphenoxy)-2,4-distearoxy-s-triazine

The preparation of the 2-chloro-4,6-distearoxy-s-triazine was carried out in the manner indicated for the 2-chlor-4,6-dilauroxy-s-triazine in Example I. Also the addition reaction with 2,6-diphenyl hydroquinone was also performed in the same manner as Examples I and II. The resulting reaction product had a melting point of 33° C.

EXAMPLE IV

In the following table the results of a number of comparative experiments are listed. In the experiments the induction times of a number of polypropylene films having different stabilizer compositions were determined.

| Run | Primary antioxidant 0.1% by weight according to invention | Temperature 140° C. primary antioxidant | Temperature 140° C. primary antioxidant plus 0.25% DLTDP | Temperature 140° C. primary antioxidant plus 0.25% DSTDP | Temperature 120° C. primary antioxidant | Temperature 120° C. primary antioxidant plus 0.25% DLTDP | Temperature 120° C. primary antioxidant plus 0.25% DSTDP |
|---|---|---|---|---|---|---|---|
| 1 | | — | 20 | 15 | — | 260 | 150 |
| 2 | $R_1 = R_2 =$ phenyl $R_4 = R_5 =$ lauryl($C_{12}H_{25}$) | 15 | 480 | 1700 | 80 | 1320 | 5700 |
| 3 | $R_1 = R_2 =$ tert.butyl $R_4 = R_5 =$ lauryl($C_{12}H_{25}$) | | 700 | | | | 3200 |
| 4 | $R_1 =$ phenyl; $R_2 =$ tert. butyl $R_4 = R_5 =$ lauryl($C_{12}H_{25}$) | 15 | 650 | 2000 | 90 | 1250 | 3800 |
| 5 | $R_1 = R_2 =$ phenyl $R_4 = R_5 =$ stearyl($C_{18}H_{37}$) | 8 | 490 | 1600 | 20 | 1580 | 5900 |
| 6 | $R_1 =$ phenyl; $R_2 =$ tert. butyl $R_4 = R_5 =$ stearyl($C_{18}H_{37}$) | 16 | 640 | 2200 | 70 | 1350 | 5000 |
| 7 | Irganox 1010 | 1150 | 1500 | 1730 | 2700 | 3600 | 3400 |

The above table clearly shows that the primary antioxidants according to the present invention made it possible to obtain satisfactory results when combined with a secondary antioxidant. It also follows that the use of DSTDP leads to considerably better results than the use of DLTDP thus demonstrating the advantage of a non-volatile compound with a relatively long alkyl group. As a primary antioxidant it is clearly preferable to use the ortho-phenyl substituted compound, which makes it possible in many cases to obtain a far higher activity per unit weight than the known Irganox 1010 which is often used under similar conditions.

We claim:

1. A composition comprising a compound of the formula,

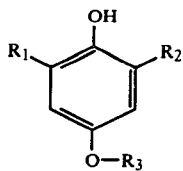

wherein $R_1$ is selected from the group consisting of tertiary butyl, isopropyl, cyclohexyl, and phenyl, $R_2$ is selected from the group consisting of cyclohexyl and phenyl, and $R_3$ is a substituted triazine of the formula,

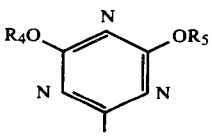

wherein $R_4$ and $R_5$ independently are selected from the group consisting of alkyl groups containing 8 to 20 carbon atoms and a secondary antioxidant selected from the group consisting of β-activated thio ethers, phosphites, and thiophosphites.

2. The composition of claim 1 wherein the secondary antioxidant is distearyl thiodipropionate.

3. The composition of claim 1 wherein the weight ratio of secondary antioxidant to primary antioxidant is between 2 to 1 and 10 to 1.

4. An organic substance which is normally subject to decomposition having incorporated therein from 0.01 to 10% by weight of the composition of claim 1.

5. A composition normally subject to decomposition having incorporated therein from 0.03 to 1% by weight of the composition of claim 1.

* * * * *